(12) United States Patent
Menchaca

(10) Patent No.: US 8,997,750 B1
(45) Date of Patent: Apr. 7, 2015

(54) IMMOBILIZATION DEVICE FOR RADIATION THERAPY TREATMENT

(76) Inventor: Everardo Menchaca, Midland, MI (US)

( * ) Notice: Subject to any disclaimer, the term of this patent is extended or adjusted under 35 U.S.C. 154(b) by 139 days.

(21) Appl. No.: 13/317,708

(22) Filed: Oct. 26, 2011

(51) Int. Cl.
*A61B 19/00* (2006.01)
*A61B 17/70* (2006.01)

(52) U.S. Cl.
CPC .................................. *A61B 17/70* (2013.01)

(58) Field of Classification Search
USPC ........ 128/845, 846, 869–870; 606/70–73, 98, 606/252, 264
See application file for complete search history.

(56) References Cited

U.S. PATENT DOCUMENTS

| | | | | |
|---|---|---|---|---|
| 4,550,713 A | * | 11/1985 | Hyman | 600/21 |
| 5,620,449 A | * | 4/1997 | Faccioli et al. | 606/98 |
| 5,707,372 A | * | 1/1998 | Errico et al. | 606/252 |
| 5,766,179 A | * | 6/1998 | Faccioli et al. | 606/98 |
| 5,775,337 A | * | 7/1998 | Hauger et al. | 128/869 |
| 6,669,697 B1 | * | 12/2003 | Pisharodi | 606/264 |

* cited by examiner

*Primary Examiner* — Michael A. Brown

(57) ABSTRACT

A stabilization bar and a stabilization method for stabilizing patients during radiation therapy treatment.

3 Claims, 2 Drawing Sheets

IMMOBILIZATION DEVICE FOR RADIATION THERAPY TREATMENT

BACKGROUND OF THE INVENTION

This invention deals with a stabilization method for stabilizing patients during radiation therapy treatment.

Computed tomography, also called CT or CT scan, is a process that uses X-rays and computer technology to make cross-section images of the body. The equipment is also used for cancer radiation therapy treatment.

The totality of equipment used for this technique is very complex, but this invention deals with immobilization of a patient during use of the equipment and thus, this specification will only discuss the immobilization equipment aspect.

The patent is usually immobilized on a table which is especially constructed to accommodate immobilization devices. There are notches in the edges of the table that accommodate locator bars that can be locked in the notches of the table to help with immobilization of the patient. Such locator bars are, for example QFix, manufactured by WFR Aquaplast, Wychoff, N.J. and Exact, manufactured by Med-Tec, Orange City, Iowa.

In addition, rigid or semi-rigid foam immobilization devices are used on top of the locator bars to accommodate the person being examined, such foam immobilization devices being actually formed around the back of the patient's body prior to use in the examination or treatment.

Thus, to prepare such a device, plastic bags are filled with foam ingredients and allowed to foam within the bag around the back of the patient's body so that the patient's body form makes up the front part of the foam immobilization device. Obviously, the plastic of the plastic bag protects the patient from the foam material.

In another embodiment, there is used "vacuum bags" which are essentially a bag containing pelletized or granular material. Also, bean bags can be used in this invention. The bag is placed under a patient, formed up around the patient, and then the air is suctioned out and the air way is capped off so air stays out.

In use, the locator bar is placed underneath the bag and patient during foaming or suctioning, leaving indentions that are formed in the back of the device by protrusions that are located on the locator bar.

After the foam hardens or cures, or after the bag is capped, the device is removed from the patient with the locator bar staying with the table.

Thereafter, the device is utilized on a table for the examination by locking the locator bars into the notches of the table.

Even though these locator bars are adequately locked in the notches of the examining table, and the protrusions protrude into the bag immobilization device, the immobilization device does not do an adequate job of immobilization.

The quality of the treatment and/or the images generated by tomography equipment depends substantially on maintaining the patient's body stable, and in an exact position.

Thus, what is needed is a device and a method of assuring that the patient's body can be stable and in an exact position. The devices of this invention assure that the patient's body can be stable and in an exact position during treatment.

THE INVENTION

Thus, what is disclosed and claimed herein is one embodiment of an invention which is a combination of a locating bar and a stabilizer bar for stabilization of a bag immobilization device.

The stabilizer bar comprises a non-circular bar having a predetermined length and predetermined outside dimensions. In addition, the non-circular bar has at least one flat surface, the flat surface having at least two spaced-apart openings in it.

In a second embodiment, there is a stabilizer bar having a predetermined length and predetermined outside dimensions. The stabilizer bar has at least one flat surface and the flat surface has at least two spaced-apart openings in it.

In a third embodiment, there is a method of immobilizing a patient for medical treatment using computed tomography equipment wherein the computed tomography equipment has at least a table.

The method comprises attaching a locator bar to the computed tomography table; mounting a stabilizer bar as set forth just Supra, on the locator bar, and the placing a bag immobilization device over the stabilizer bar, and thereafter, immobilizing a patient in the immobilization device.

DETAILED DESCRIPTION OF THE INVENTION

Figure 1:
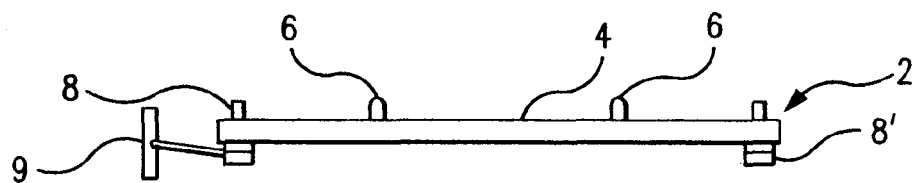
FIG. 1 is a full side view of a locator bar of the prior art.
Figure 2:
FIG. 2 is a full side view of a stabilizer bar of this invention showing the openings in phantom.

Turning now to FIG. 2, there is shown a stabilizer bar 1 of this invention. The stabilizer bar 1 is a non-circular bar having a predetermined length and predetermined outside dimensions that are determined by the type of locator bar 2 (FIG. 1) is being used in the equipment. Nominally, the length of the stabilizer bar 1 can range from about 10 inches to about 16 inches and the outside dimensions range from about ¾ inch to about 1¼ inches.

The stabilizer bar 1 can be manufactured from any one of a group of materials, such as plastics, metals, wood, carbon composites, and the like. Preferred as a metal is aluminum and preferred for plastics are acrylics, polycarbonates, polypropylene and polyethylene, including crosslinked polyethylene. Most preferred are acrylics and polycarbonates.

Figure 3:
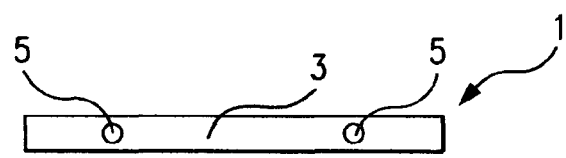
FIG. 3 is a full bottom view of a stabilizer bar of this invention showing the openings in the bottom.
Figure 4:
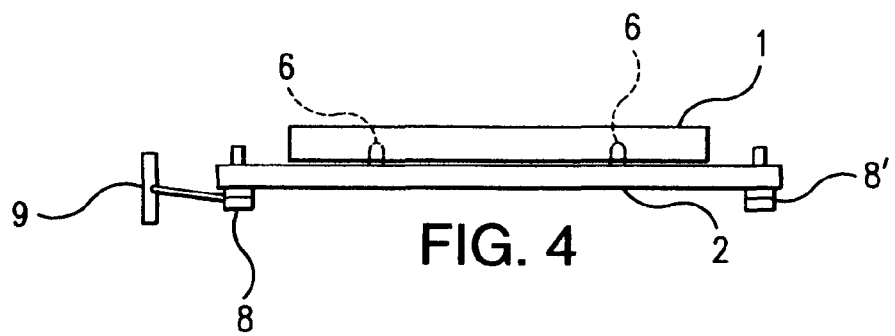
FIG. 4 is a full side view of the combination of FIG. 1 and FIG. 2.

The stabilizer bar 1 as at least one flat surface 3, that allows the stabilizer bar 1 to mate with the top surface 4 of the locator bar 2. The stabilizer bar 1 as shown in FIGS. 2 and 3 has two openings 5, however, it is contemplated within the scope of this invention to have three, four, or more such openings.

The openings 5 have a depth and a circumference that will allow the protrusions 6 of the locator bar 2 to insert freely into the openings 5.

Turning now to FIG. 1, there is shown a locator bar 2 which is a prior art locator bar. The locator bar 2 is constructed such that it will lock onto a tomography table 7, shown in FIG. 5, through the use of notches in the edge of the table (not shown) and the lock lugs 8 and 8'. The distal lock lug 8' just inserts into a notch. The near lock lug 8 has an apparatus that enables the technician to insert the lock lug 8 into the notch on that side of the table, and lock the lock lug 8 into place using the apparatus and handle 9.

Figure 5:
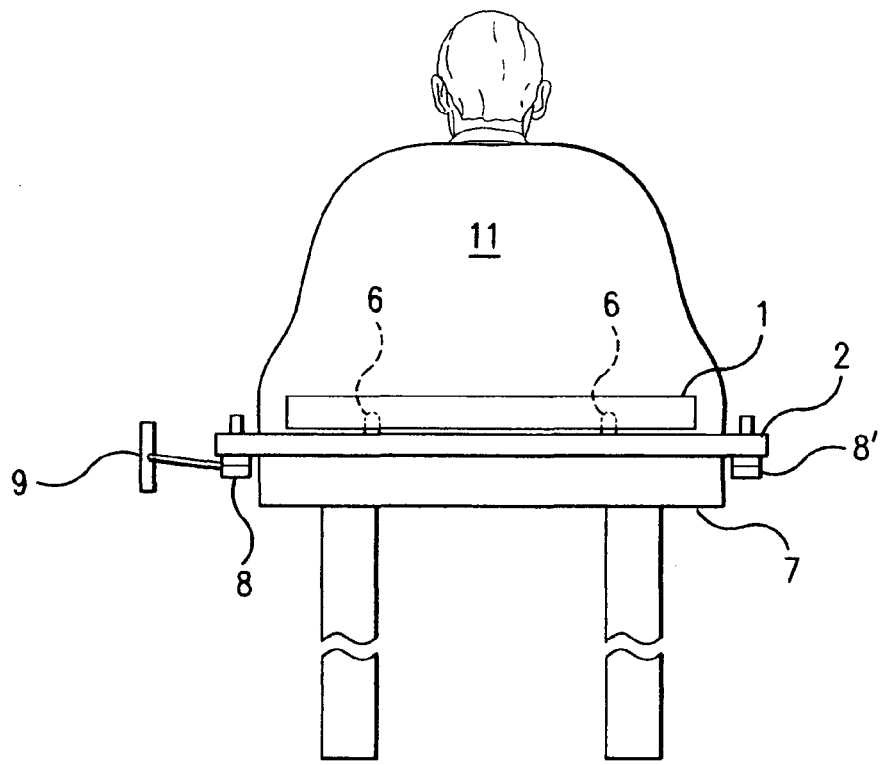
FIG. 5 is a full back view of a patient immobilized on a foam immobilization device with the combination of this invention in place on a table.

In one embodiment, the stabilizer bar 1 is molded into the foamed immobilization device 11 shown in FIG. 5. The foamed immobilization device 11, along with the molded in stabilizer bar 1, are placed down over the locator bar 2.

In another embodiment, the stabilizer bar 1 is molded into the immobilization device 12 by forming the bag 13 around the patient and then sucking the air from the bag 13. The bag 13 is then capped to hold the vacuum.

Figure 6:
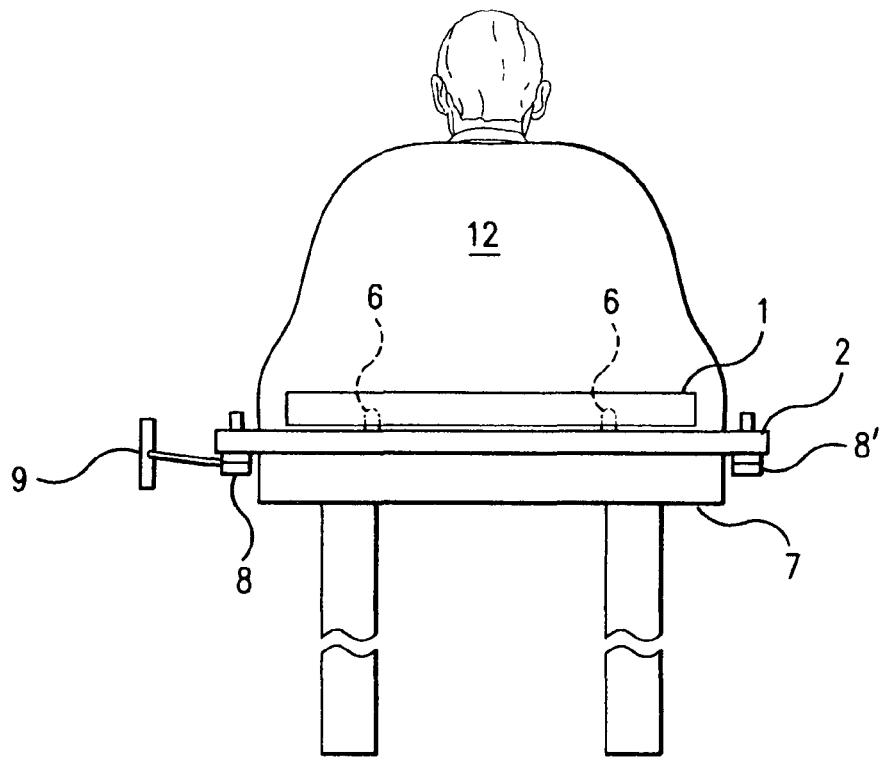
FIG. 6 is a full back view of a patient immobilized on a vacuum bag immobilization device with the combination of this invention in place on a table.

As note Supra, rigid or semi-rigid foam immobilization devices 11 (FIG. 5) and 12 (FIG. 6) are used on top of the locator bars 2 to accommodate the person being examined, such immobilization devices 11 and 12 being actually formed around the back of the patient's body prior to use in the examination or treatment, however in this invention, the immobilization devices 11 and 12 are formed down over the stabilizer bar 1 and the locator bar 2.

Thus, to prepare such a foamed immobilization device 11, plastic bags are filled with foam ingredients and allowed to foam within the bag around the back of the patient's body so that the patient's body form makes up the front part of the foam immobilization device 11. Obviously, the plastic of the plastic bag protects the patient from the foam material.

The locator bar 2 surmounted by the stabilizer bar 1 is placed underneath the plastic bag and patient during foaming thus allowing the foam to form over the stabilizer bar 1 and the locator bar 2.

After the foam hardens or cures, the foamed immobilization device 11 is removed from the patient with the locator bar 2 staying on the table and the stabilizer bar 1 intact in the back of the foamed immobilization device 11.

Thus, in order to utilize the devices of this invention, there is a method of immobilizing a patient for medical treatment using computed tomography equipment wherein the computed tomography equipment has at least a table 7 (FIG. 5).

The method comprises attaching a locator bar 2 to the computed tomography table 7, mounting stabilizer bar 1 on the locator bar 2, and thereafter, placing an immobilization device 11 or 12 over the stabilizer bar 1 and placing the patient in the immobilization device 11 or 12.

What is claimed is:

1. A method of immobilizing a patient's body for radiation therapy medical treatment using computed tomography equipment wherein said computed tomography equipment has at least a table, said method comprising:
   i attaching a locator bar to said computed tomography table;
   ii mounting a stabilizer bar on said locator bar said stabilizer bar having a predetermined length and predetermined outside dimensions, said stabilizer bar having at least one flat surface and said flat surface having at least two spaced-apart openings therein;
   iii placing an immobilization device over said stabilizer bar;
   iv placing said patient's body in said immobilization device.

2. A method as claimed in claim 1 wherein the immobilization device is a foamed immobilization device.

3. A method as claimed in claim 1 wherein the immobilization device is a vacuum bag.

* * * * *